United States Patent [19]
Bates

[11] Patent Number: 5,935,139
[45] Date of Patent: *Aug. 10, 1999

[54] SYSTEM FOR IMMOBILIZING OR MANIPULATING AN OBJECT IN A TRACT

[75] Inventor: James S. Bates, Bloomington, Ind.

[73] Assignee: Boston Scientific Corporation, Natick, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/642,756

[22] Filed: May 3, 1996

[51] Int. Cl.$^6$ .................................................. A61M 25/00
[52] U.S. Cl. ............................... 606/159; 600/1; 600/200
[58] Field of Search ................................. 606/127, 128, 606/106, 159, 170, 198, 200; 604/96; 623/1, 12

[56] References Cited

U.S. PATENT DOCUMENTS

| | | |
|---|---|---|
| 3,996,938 | 12/1976 | Clark, III . |
| 4,425,908 | 1/1984 | Simon . |
| 4,447,227 | 5/1984 | Kotsanis ..................................... 604/96 |
| 4,590,938 | 5/1986 | Segura et al. . |
| 4,650,466 | 3/1987 | Luther . |
| 4,706,671 | 11/1987 | Weinrib . |
| 4,723,549 | 2/1988 | Wholey et al. . |
| 4,728,319 | 3/1988 | Masch . |
| 4,790,812 | 12/1988 | Hawkins, Jr. et al. . |
| 4,790,813 | 12/1988 | Kensey . |
| 4,794,928 | 1/1989 | Kletschka . |
| 4,873,978 | 10/1989 | Ginsburg . |
| 4,885,003 | 12/1989 | Hillstead . |
| 4,926,858 | 5/1990 | Gifford, III et al. . |
| 4,998,539 | 3/1991 | Delsanti .................................. 606/194 |
| 5,011,488 | 4/1991 | Ginsburg . |
| 5,041,093 | 8/1991 | Chu . |
| 5,053,008 | 10/1991 | Bajaj ....................................... 606/200 |
| 5,071,407 | 12/1991 | Termin et al. . |
| 5,100,423 | 3/1992 | Fearnot . |
| 5,102,415 | 4/1992 | Guenther et al. ......................... 604/96 |
| 5,192,286 | 3/1993 | Phan et al. . |

(List continued on next page.)

FOREIGN PATENT DOCUMENTS

| | | |
|---|---|---|
| 0 737 450 A1 | 10/1996 | European Pat. Off. . |
| 2821048 | 11/1979 | Germany . |
| 2 020 557 | 11/1979 | United Kingdom . |
| WO 91/11209 | 8/1991 | WIPO . |
| WO 94/24946 | 11/1994 | WIPO . |
| WO 96/01591 | 1/1996 | WIPO . |

OTHER PUBLICATIONS

*The Journal of Invasive Cardiology*, vol. 8, Supplement E, 1996, "Stents Don't Require Systemic Anticoagulation . . . But the Technique (and Results) Must Be Optimal", by Issaam Moussa, MD, et al., pp. 3E–30E, Health Management Publications, Inc.

Vorwerk et al., "Percutaneous Embolectomy; In Vitro Investigations of the Self–expanding Tulip Sheath[1]", Radiology, (1992), 182: 415–418.

Vorwerk et al., "Percutaneous Balloon Embolectomy with a Self–expanding Tulip Sheath: In Vivo Experiments", Radiology, (1995), 197: 153–156.

*Primary Examiner*—Michael Buiz
*Assistant Examiner*—William W. Lewis
*Attorney, Agent, or Firm*—Testa, Hurwitz & Thibeault, LLP

[57] ABSTRACT

A sheath defines a lumen. A mesh portion is coupled to the sheath and is movable between a retracted position and an expanded position. An elongate member is disposed in the lumen and is operably attached to one of the mesh portion and the sheath such that longitudinal movement of the elongate member within the lumen causes movement of the mesh portion between the expanded position and the retracted position. The sheath and the mesh portion are introduced into the body along with an end effectuator. The mesh portion is moved to its expanded position to form an object supporting surface. The surface is used to support an object, such as a stone, during a medical treatment procedure using the end effectuator.

20 Claims, 7 Drawing Sheets

U.S. PATENT DOCUMENTS

| | | |
|---|---|---|
| 5,329,942 | 7/1994 | Gunther et al. . |
| 5,354,310 | 10/1994 | Garnic et al. .......................... 606/198 |
| 5,376,100 | 12/1994 | Lefebvre . |
| 5,380,273 | 1/1995 | Dubrul et al. . |
| 5,421,832 | 6/1995 | Lefebvre . |
| 5,549,626 | 8/1996 | Miller et al. . |
| 5,713,848 | 2/1998 | Dubrul et al. . |

SYSTEM FOR IMMOBILIZING OR MANIPULATING AN OBJECT IN A TRACT

U.S. Pat. No. 5,160,336, entitled "DEVICE FOR ACTING BY ULTRASONIC VIBRATIONS ON AN OBJECT," is incorporated herein by reference.

BACKGROUND OF THE INVENTION

The present invention deals with a system for treating an object in a body tract. More specifically, the present invention deals with a system for immobilizing or manipulating an object, such as a stone, to better accommodate treatment of the object.

Objects, such as stones, can reside in the kidney, ureter, or biliary duct. Such stones can be extremely painful and require medical treatment. Removal of such stones has been accomplished by two methods in the past. The first method is removal through conventional surgery. Such a treatment has obvious disadvantages, risks and drawbacks. The second method is removal under the guidance of an endoscope. A grasping device is guided through the bodily tract to the site of the stone and is used to grasp and remove the stone under endoscopic guidance. Examples of grasping devices which have been used in the past for the removal of stones include forceps with axially-directed grasping arms, and basket devices such as shown in the Segura et al. U.S. Pat. No. 4,590,938.

Another prior means of treating stones includes directing a force against the stone within the duct to break the stone into pieces so that it can be more easily passed or removed. There are currently many different methods employed to direct force against a stone. One such method is set out in U.S. Pat. No. 5,160,336, entitled "DEVICE FOR ACTING BY ULTRASONIC VIBRATIONS ON AN OBJECT," which is incorporated by reference herein. In order to more efficiently break the stone, attempts have been made to immobilize the stone while the breaking force is imparted on the stone. This provides a more efficient system because the energy directed toward the stone during application of the breaking force is not dissipated through movement of the stone. Instead, the stone is forced to absorb a greater portion of the energy and thereby break more readily.

Prior attempts to immobilize the stone during treatment have included placing an inflatable balloon behind the stone in the duct to provide a "backstop" for the stone. However, such balloons require inflation lumens, seals, relatively time consuming inflation and deflation steps, and are sensitive to inflation pressures. The balloons are susceptible to puncture or rupture which is undesirable. Further, the balloons completely occlude the ureter (or other bodily passage) which can also have disadvantages. In addition, the balloons provide an extremely elastic backstop so that an undesirably high amount of the force imparted on the stone is dissipated in the elasticity of the balloon.

Another method of immobilizing the stone during treatment has been to use a basket, such as that set out in U.S. Pat. No. 4,590,938. The treating physician captures the stone in the basket and then attempts to break the stone into pieces. However, such baskets do not provide efficient filtering in that smaller stone particles can slip through the basket. In addition, such baskets, in order to immobilize the stone, must be positioned around the stone. This reduces access to the surface of the stone by any other end effectuating device such as a treating laser or probe. This tends to make the operation more difficult and increases the potential risk of damage to the tract. Further, crushing baskets which are sometimes used to crush gall stones cannot be practically used in the urinary tract to crush kidney stones because of the great amount of crushing force which is required. Attempting to exert such force on a kidney stone with a crushing basket would substantially increase the risk of damage to the urinary tract.

SUMMARY OF THE INVENTION

A sheath defines a lumen. A mesh portion is coupled to the sheath and is movable between a retracted position and an expanded position. An elongate member is disposed in the lumen and is operably attached to one of the mesh portion and the sheath such that longitudinal movement of the elongate member within the lumen causes movement of the mesh portion between the expanded position and the retracted position. The sheath and the mesh portion are introduced into the body. The mesh portion is advanced to an area to be treated. The mesh portion is moved to its expanded position to form an object supporting surface. The surface is used to support an object, such as a stone.

DETAILED DESCRIPTION OF THE PREFERRED EMBODIMENTS

Figure 1:
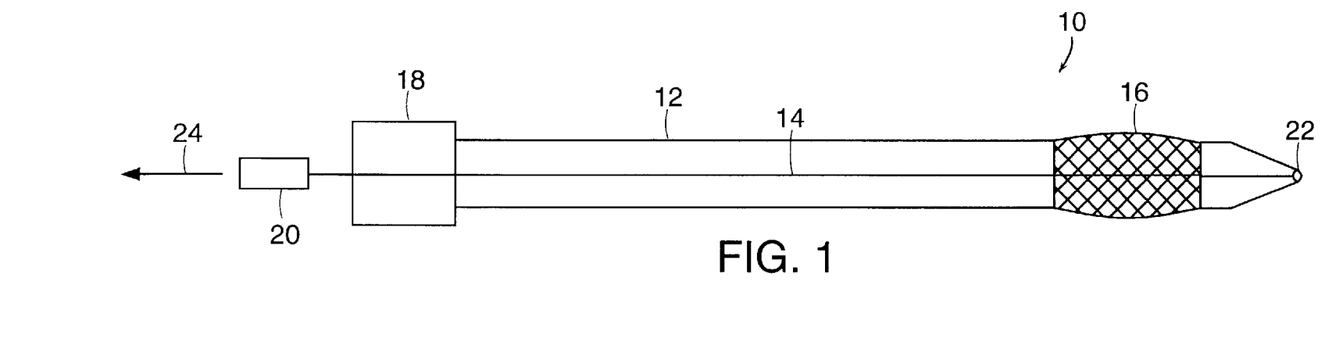
FIG. 1 is a side view of an expandable device according to the present invention.

FIG. 1 illustrates an expandable device 10 according to the present invention. In the embodiment shown in FIG. 1, expandable device 10 includes a sheath or catheter 12, cannula 14 and mesh portion 16.

Catheter 12 preferably has, at its proximal end, a handle 18. Cannula 14 is also provided, at its proximal end, with a handle 20.

Catheter 12 is preferably made of commonly available materials which provide sufficient strength and springiness for adequate operation, but which are soft enough to avoid substantial trauma or irritation to the tract or duct in which catheter 12 is deployed. Materials which may commonly be used to form catheter 12 include polyethylene, nylons, Pebax, Teflon, urethanes, silicones, and other suitable polymer materials. The material is preferably biocompatable and inert to body fluids.

In the preferred embodiment, cannula 14 is a stainless steel tube or may simply be a solid wire or a coil which extends the entire length of catheter 12 and is connected to the interior of a distal tip 22. Cannula 14 is axially movable within the lumen of catheter 12.

Mesh portion 16, in the preferred embodiment, is simply an expandable element which allows fluid flow therethrough and is preferably formed of a deformable mesh or net material, or of braided or woven fibers or metal wires, but can also be formed of a plurality of spirally arranged wires or fibers. The material is preferably formed of polymer fibers, such as nylon. In the embodiment in which mesh portion 16 is formed of a polymer mesh or netting material, the mesh size is preferably very small, and the holes in the meshing are on the order of several thousandths of an inch. It has been found that such a relatively tight mesh allows the passage of fluid therethrough, but does not allow any substantial particulate passage therethrough. In one preferred embodiment, a mesh net is formed wherein each strand of the mesh net is approximately 0.005 inches in diameter and the foramina in the net are several thousandths of an inch (e.g., 0.001 to 0.010 inches) across.

In the embodiment in which mesh portion 16 is formed of metal wires, the wires preferably comprise 0.006 inch diameter stainless steel wires. There are preferably at least three wires worked into overlapping spiral patterns. This is shown and discussed in greater detail with respect to FIGS. 5B and 5C.

Mesh portion 16 is expandable in a radial direction by manipulating cannula 14 relative to catheter 12. For instance, if cannula 14 is partially withdrawn from catheter 12 in the direction indicated by arrow 24, tip 22 is drawn closer to sheath 12 thereby exerting a compressive force on mesh portion 16. This causes mesh portion 16 to bulge outwardly in the radial direction. The further tip portion 22 is brought toward sheath 12, the greater is the radial outward displacement of mesh portion 16.

Figure 2:
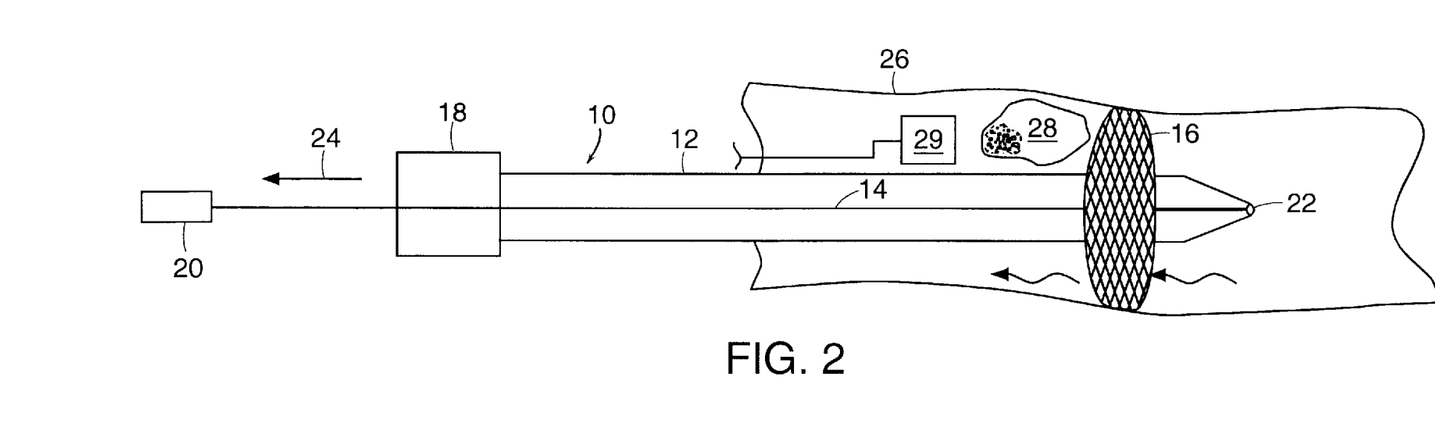
FIG. 2 is a side view of the expandable device of FIG. 1 deployed in a duct or tract or vessel of a body.

FIG. 2 illustrates expandable device 10 deployed in a duct or tract 26 of a body. Similar items are similarly numbered to those shown in FIG. 1. FIG. 2 also shows an object, such as a kidney stone or a gall stone 28, which resides in tract 26. In order to remove stone 28, expandable device 10 is used.

Expandable device 10 is first introduced (such as through a proper scope) into the duct in the retracted profile position shown in FIG. 1. After mesh portion 16 has been advanced to a desired point, preferably beyond stone 28, and preferably under endoscopic observation or guidance, handle 20 of cannula 14 is withdrawn from catheter 12 in the direction indicated by arrow 24. This causes tip 22 to move toward sheath 12 and thereby exert a compressive force on mesh portion 16. Mesh portion 16 bulges radially outwardly. Handle 20 is withdrawn from catheter 12 until the diameter of mesh portion 16 reaches a desired dimension. Typically, this dimension roughly corresponds to the lumen dimension of tract 26 so the outer periphery of mesh portion 16 contacts the inner periphery of tract 26. Mesh portion 16 thus provides a backstop, or immobilization surface, for stone 28.

After being so deployed, another instrument, such as a ballistic jack hammer-type instrument, a laser, or other treatment device 29, is inserted closely adjacent stone 28 and is used to break stone 28 into fragments. Mesh portion 16 provides a relatively rigid backstop so that a large amount of the force imparted on stone 28 is absorbed by stone 28 and is actually used in breaking stone 28, rather than being dissipated in the backstop material. It should also be noted that mesh portion 16, when in the expanded position shown in FIG. 2, provides a substantially disk-shaped object supporting surface which is used to support stone 28. This leaves the vast majority of the surface of stone 28 accessible by the instrument being used to break stone 28.

Once stone 28 is broken into pieces or fragments, those fragments are removed in any number of suitable ways. For instance, baskets can be deployed to remove the fragments. However, expandable device 10 is also useful in removing the fragments, or in sweeping the tract 26. Once stone 28 is broken into fragments, mesh portion 16 is preferably maintained in the expanded position and expandable device 10 is withdrawn from tract 26. Since mesh portion 16 is formed of a mesh size which allows fluid flow therethrough, but which does not allow any substantial particulate flow therethrough, this has the effect of sweeping tract 26 substantially clean of stone fragments.

Mesh portion 16 can also be formed to assume a substantially predetermined configuration upon being expanded. For example, the fibers in a woven mesh or net can be woven such that, when the compressive force is exerted on mesh portion 16 by sheath 12 and tip 22, the resultant expansion yields a predetermined configuration. Further, where mesh portion 16 is formed of heatsettable or other suitable polymer materials, those materials can be heatset or thermoset so that they obtain a predetermined configuration upon expansion.

Figure 3:
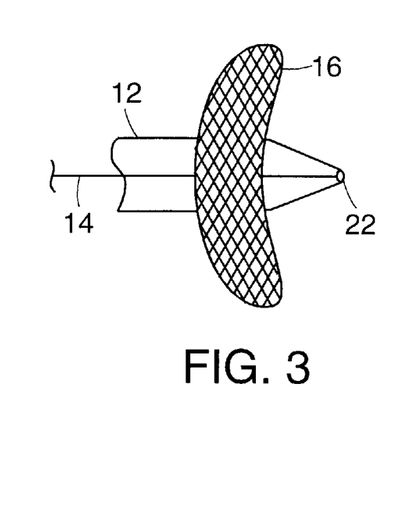
FIGS. 3 and 4 illustrate different configurations obtainable using the expandable device according to the present invention.
Figure 4:
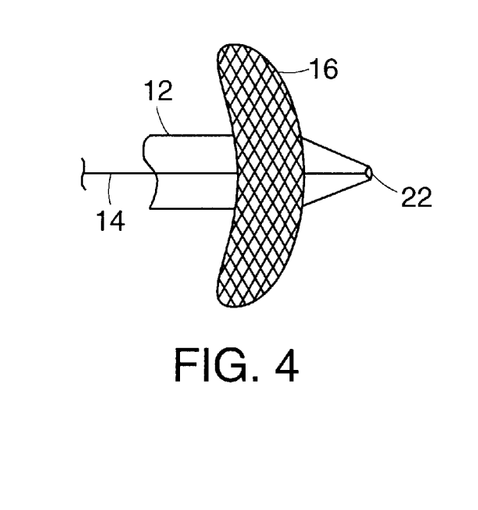

FIGS. 3 and 4 illustrate two preferred predetermined configurations. In FIG. 3, mesh portion 16 is expanded to assume a substantially concave configuration relative to tip 22. This, in some instances, is beneficial or advantageous such as when expandable device 10 is used to sweep or filter a duct or tract 26. FIG. 4 illustrates that mesh portion 16 assumes a substantially convex shape relative to tip 22. This is beneficial when expandable device 10 is used in removing stones from a duct or tract 26. For instance, in certain instances, stones can become impacted in the side tissue of a duct or tract 26. In such an instance, the shape of mesh portion 16 shown in FIG. 4 is useful in scraping or digging the stones out of the tissue defining the duct or tract. It should be noted, however, that in both FIG. 3 and FIG. 4, the shape assumed by mesh portion 16 is only a fairly shallow dish or bowl shape. This allows mesh portion 16 to provide a stone supporting or immobilization surface which still allows a great deal of access to the surface of stone 28. Therefore, if a device is introduced to break stone 28, access to stone 28 is substantially uninhibited by mesh portion 16.

Figure 5A:
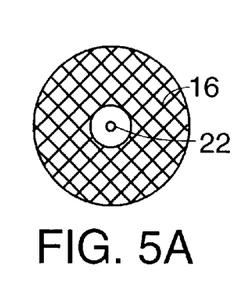
FIG. 5A shows an end view of the expandable device according to the present invention.

FIG. 5A illustrates an end view of mesh portion 16 when deployed in its expanded position. FIG. 5A shows that the preferred configuration of mesh portion 16 is substantially circular, or is a shape which is suitable to substantially conform to the interior of the duct or tract 26 in which mesh portion 16 is being deployed.

Figure 5B:
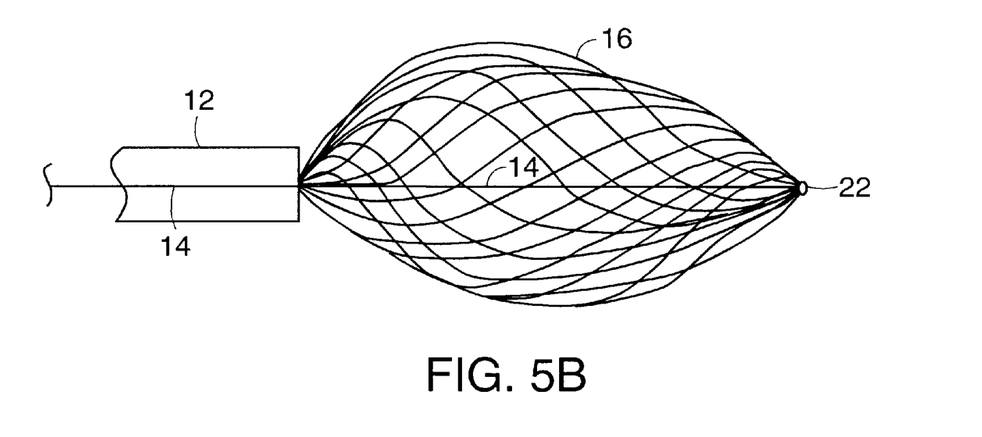
FIGS. 5B and 5C illustrate another embodiment of the present invention.
Figure 5C:
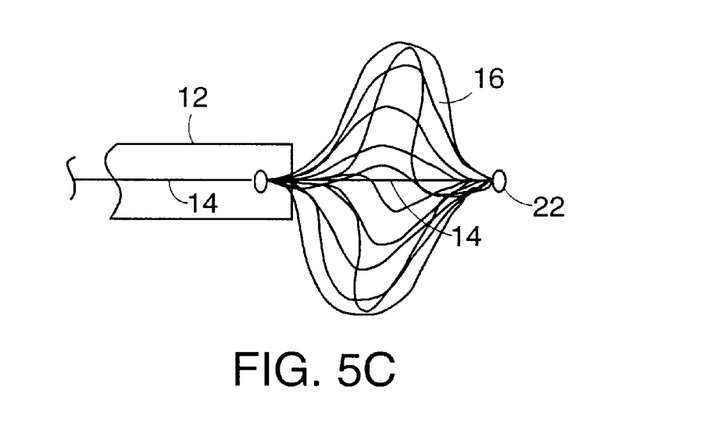

FIG. 5B illustrates mesh portion 16 formed of a plurality of spirally arranged wires or fibers. FIG. 5C illustrates the shape of mesh portion 16 in the expanded position.

Figure 5D:
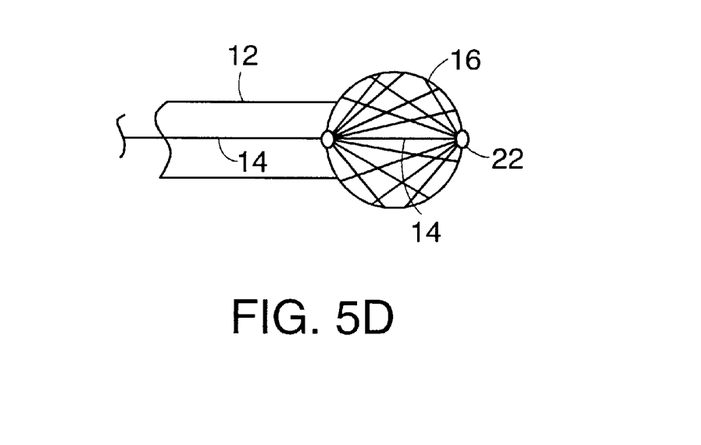
FIGS. 5D–5H illustrate other embodiments of the present invention.
Figure 5E:
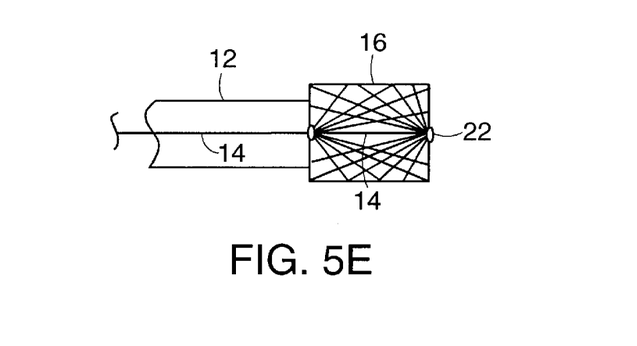
Figure 5F:
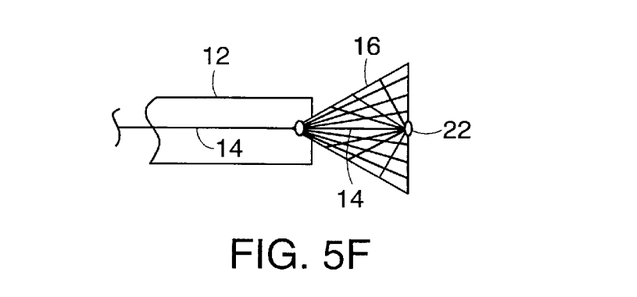

FIGS. 5D, 5E, 5F, 5G and 5H also show alternative predetermined shapes for mesh portion 16 in the expanded position. FIG. 5D shows a generally spherical shape. FIG. 5E shows a substantially square or rectangular box shape and FIG. 5F shows a pyramid or cone shape which can have a substantially square or curved base cross-section. FIGS.

Figure 5G:
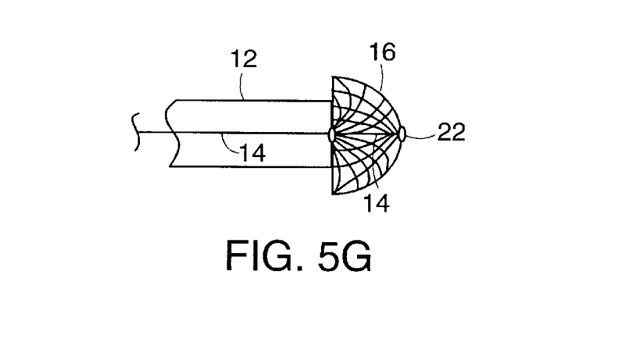
Figure 5H:
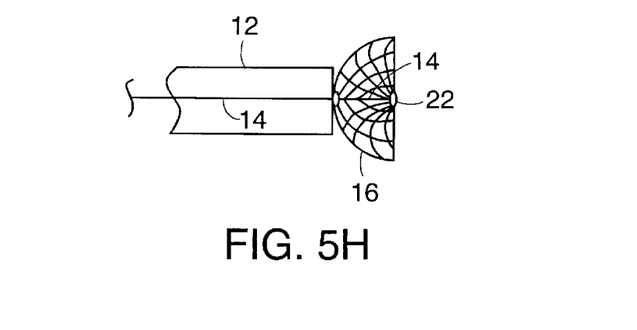

5G and 5H show a hemispherical shape directed toward, and away from, lip 22. All of these shapes of mesh portion 16 can have concave or convex surfaces, as desired, and can be made of mesh netting, woven or braided fibers or wires, or any other suitable materials. Any other suitable shapes can also be used.

Figure 6:
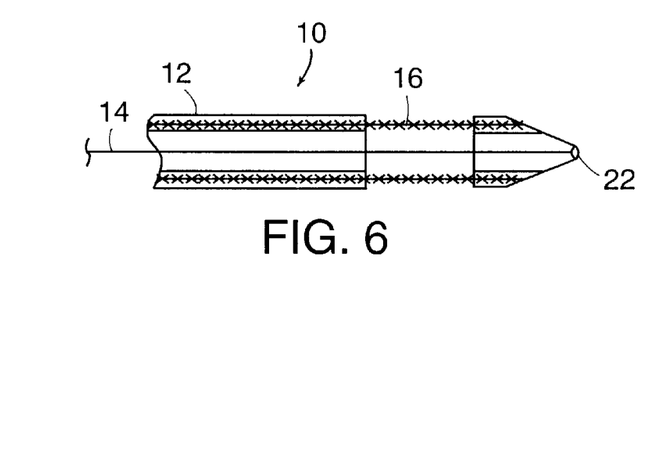
FIG. 6 illustrates one embodiment of the present invention wherein the expandable element is formed by embedding material in a sheath.

FIG. 6 is a cross-sectional view of another embodiment of expandable device 10. In some applications of expandable device 10, the outer diameter of expandable device 10 is crucial. In such applications, it is advantageous to provide mesh portion 16 embedded within the material defining catheter 12. When using this embodiment, no separate means are required to attach mesh portion 16 to the outer or inner surface of sheath 12. Therefore, any radial dimension which is added by such attachment means is eliminated.

FIG. 6 shows that mesh portion 16 is formed of a mesh material which runs substantially the entire length of catheter 12 and is embedded therein. This can be accomplished by a multiple-extrusion process in which an inner first layer of the material forming catheter 12 is extruded, mesh material forming mesh portion 16 is disposed on the first extrusion, and then a second extrusion of material forming catheter 12 is performed to cover mesh portion 16 in all areas except where it is desired that mesh portion 16 be radially expandable. It should also be noted, however, that mesh portion 16 can be embedded in the material forming catheter 12 by simply taking a shorter length of mesh portion 16 and melting it into the wall of catheter 12.

In other applications, mesh portion 16 is simply secured to sheath 12 using commonly known bonding methods for metals and plastics such as ultrasonic welding or adhesives.

Figure 7:
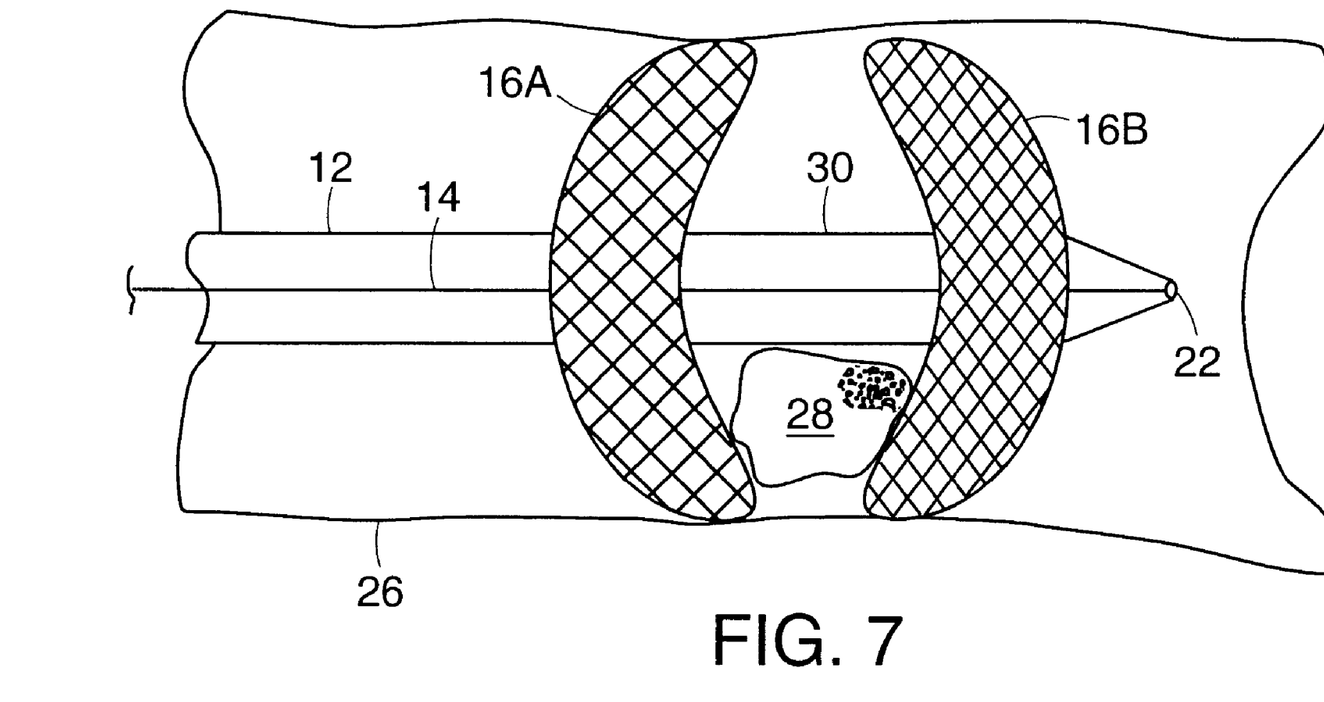
FIG. 7 illustrates another embodiment of an expandable device according to the present invention.

FIG. 7 shows another embodiment of expandable device 10 according to the present invention. In FIG. 7, expandable device 10 is provided with two mesh portions 16A and 16B. Each of mesh portions 16A and 16B is formed substantially the same as mesh portion 16 described with respect to FIGS. 1–6. However, mesh portions 16A and 16B are separated by a spacer 30. In the preferred embodiment, spacer 30 is formed of the same material as catheter 12 and is simply a generally tubular member disposed between mesh portions 16A and 16B. In such an embodiment, retraction of cannula 14 relative to catheter 12 causes a compressive force to be exerted both on mesh portion 16A and mesh portion 16B, through spacer 30. This causes both mesh portions 16A and 16B to expand radially outwardly. In the embodiment shown in FIG. 7, mesh portions 16A and 16B, when expanded, provide generally opposing object support surfaces which are shown capturing or supporting a stone 28 therebetween. Of course, any appropriate expanded configuration can be obtained with mesh portions 16A and 16B. Further, two wires such as cannula 14 can be provided to accomplish independent expansion of mesh portions 16A and 16B. While FIG. 7 shows mesh portions 16A and 16B simply trapping and holding stone 28, it should be noted that it is still possible to place an end effectuating device closely adjacent one of the mesh portions 16A and 16B to treat stone 28 through the mesh portion.

FIGS. 8A–8D illustrate yet another embodiment of the present invention. In FIGS. 8A–8D, expandable device 10 is disposed within a movable outer catheter sheath 32. Outer sheath 32 preferably extends for a major portion of the length of expandable device 10 and is axially slidable along the outer periphery of expandable device 10. Outer sheath 32 is preferably formed of a material similar to sheath 12 and has, disposed at its proximal end, a handle 34. However, outer sheath 32 may be only a relatively short sheath (on the order of the axial length of mesh portion 16) having its axial movement controlled by other means (other than handle 34) such as a control wire or a coil. Sheath 32 can be manipulated relative to expandable device 10 to obtain a desired, and controlled, radial expansion of mesh portion 16.

Figures 8A, 8B, 8D:
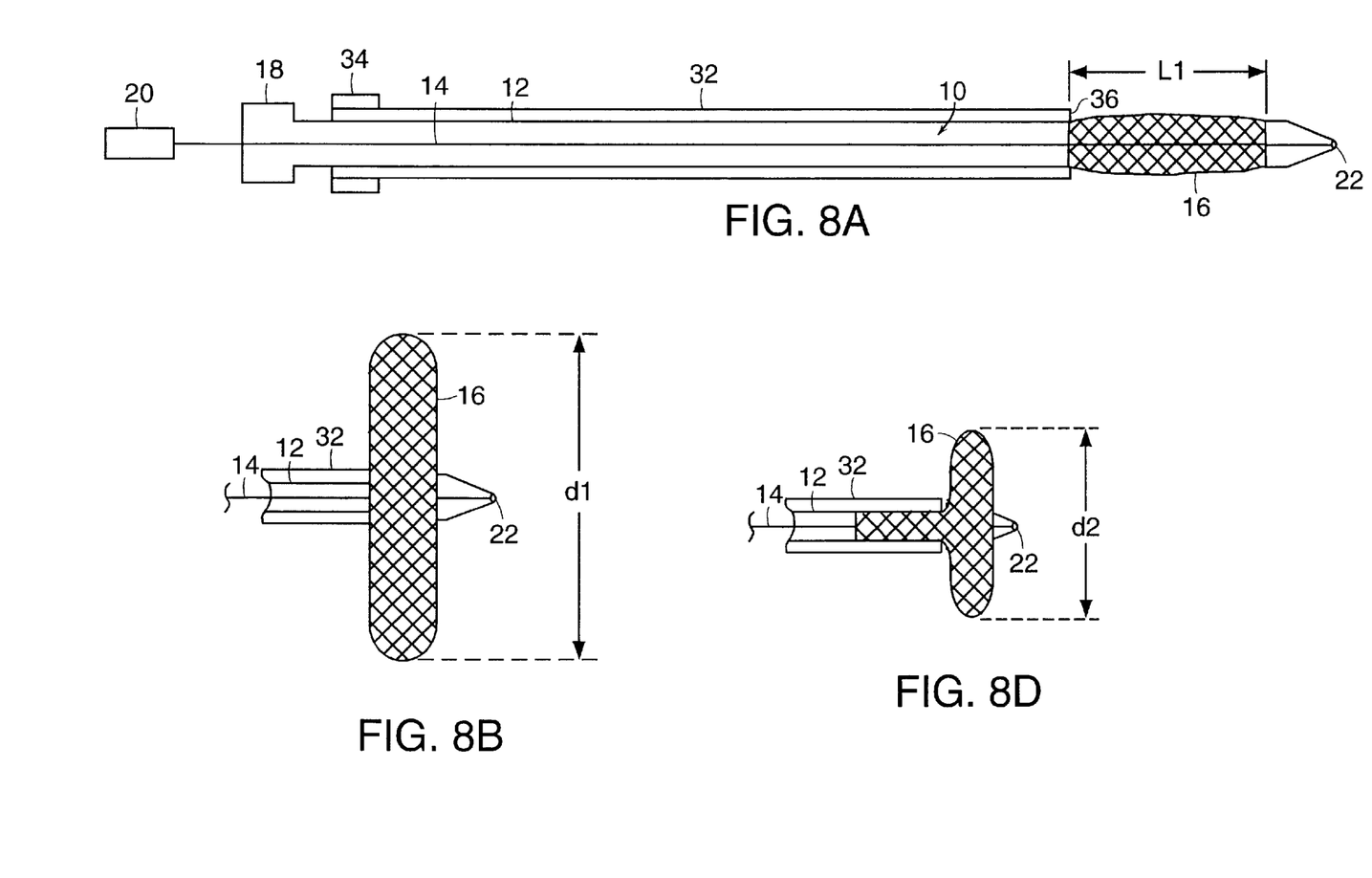
FIGS. 8A, 8B, 8C and 8D illustrate another embodiment of an expandable device according to the present invention in which the expanded diameter of the expandable element is variable.

In the embodiment shown in FIG. 8A, mesh portion 16 has an overall axial length Li. When outer sheath 32 is placed so that its distal end 36 is coterminus with the distal end of catheter 12 (as shown in FIG. 8A) the entire length Li of mesh portion 16 is available for expansion. Therefore, when cannula 14 is withdrawn relative to catheter 12, and when tip 22 and the distal end of catheter 12 exert a compressive force on mesh portion 16, mesh portion 16 is free to expand throughout its entire length. This results in an expanded configuration, such as that shown in FIG. 8B, which has a diameter d1.

Figure 8C:
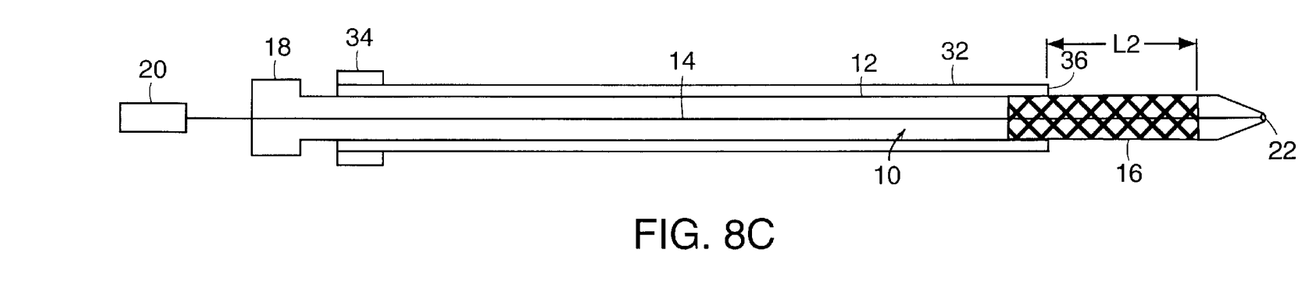

However, where it is desired that the diameter of the expanded portion be reduced, outer sheath 32 is moved axially relative to expandable device 10 to cover a portion of mesh portion 16. This is shown in FIG. 8C. Therefore, with outer sheath 32 deployed as shown in FIG. 8C, a smaller part of mesh portion 16 (having length L2) is available for radial expansion. When cannula 14 is withdrawn relative to catheter 12 to cause mesh portion 16 to expand, the expanded configuration obtained by mesh portion 16 has a diameter d2 (shown in FIG. 8D) which is smaller than the diameter d1 (shown in FIG. 8B). Of course, the diameter of the expanded configuration of mesh portion 16 can be continuously varied simply by varying the degree to which outer sheath 32 overlaps, and thereby constrains the expansion of, mesh portion 16. Sheath 32 could also be located distally of mesh portion 16 and pulled over mesh portion 16, and pushed to expose mesh portion 16.

Figure 9A:
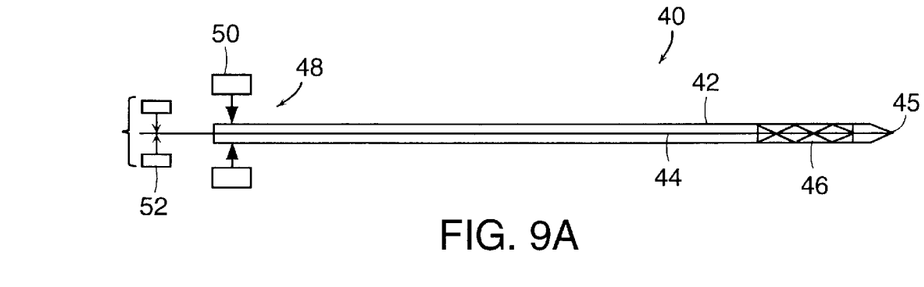
FIG. 9A illustrates another embodiment of the present invention in which the expandable element is formed in a guide wire with detachable proximal handles.
Figure 9B:
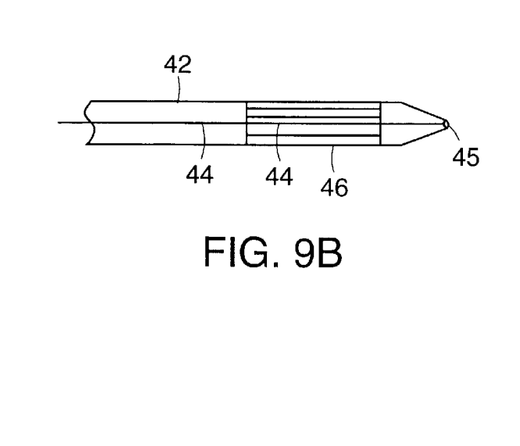
FIGS. 9B and 9C illustrate another embodiment of the present invention in the form of a guidewire.
Figure 9C:
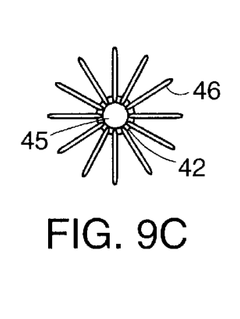

FIGS. 9A–9C show yet another preferred embodiment of the present invention. In the embodiment shown in FIG. 9A, expandable device 40 is formed, in large part, as a conventional guide wire. Expandable device 40 includes an outer sheath 42 (which is often a coil) and an inner core 44 which is coupled at a distal tip 45 to outer coil 42. As with conventional guide wires, inner core 44 is movable relative to outer coil 42. However, unlike conventional guide wires, outer coil 42 is also provided with mesh or expandable portion 46. In the embodiment shown in FIG. 9A, mesh portion 46 is formed of braided fibers or wires or of mesh netting material. In another preferred embodiment shown in FIGS. 9B and 9C, mesh portion 46 can simply be comprised of straightened or substantially linear wires which, when inner core 44 is withdrawn relative to coil 42, bulge outwardly to form an object supporting surface for supporting an object (such as a stone) in a body tract. FIG. 9C shows an end view of the mesh portion 46 of FIG. 9B in the expanded position.

For expandable device 40 to operate both as a guide wire, and as an expandable device, the proximal end 48 of expandable device 40 is provided with removable handles 50 and 52. Handle 50 is preferably a snap-on handle which can be releasably secured about the outer periphery of outer coil 42. In addition, handle 52 is preferably a handle which can be releasably secured about the outer periphery of inner core 44.

The present invention will preferably be formed with one of any number of outer diameters, but will most commonly have an outer diameter of 1.5 French to 10 French. In addition, the total length of the mesh portion will have any suitable dimension, but is preferably approximately 1–3 cm in length.

While it has been disclosed that the mesh portion of the present invention is expanded to immobilize stones or objects to prevent migration of those objects during various therapies, the present invention can also be used to manipulate or remove such objects. However, immobilization is typically used during pneumatic, mechanical, electrical, hydraulic, laser, or other forms of treatment of the stone. Further, it should be noted that the wires or fibers forming mesh portion 16 can have any suitable crosssection, such as flat wires, round wires or whatever is deemed appropriate. Since a low profile device is preferred in some applications, mesh portion 16 will be formed using as few wire crossovers (if any) as practicable in such applications, while still maintaining desired stiffness for an adequate backstop. Further, the present invention can be implemented in a multi-lumen catheter which can be used to deliver fluids, such as contrast fluid, saline-flushing fluid or caustic fluid which helps to break down the stone.

Although the present invention has been described with reference to preferred embodiments, workers skilled in the art will recognize that changes may be made in form and detail without departing from the spirit and scope of the invention.

What is claimed is:

1. A method of treating an object in a body tract, comprising:
    providing a catheter comprising:
        a sheath defining a lumen therethrough and having a first end and a second end;
        a mesh portion, coupled to the sheath, the mesh portion having first and second longitudinal ends and an intermediate portion longitudinally between the first and second ends, and being movable between a retracted position and an expanded position, the intermediate portion being displaced radially outwardly relative to the first and second longitudinal ends when the mesh portion is in the expanded position;
        an elongate member disposed in the lumen and operably attached to at least one of the mesh portion and the sheath such that axial movement of the elongate member within the lumen causes movement of the mesh portion between the retracted position and the expanded position;
    introducing the sheath and the mesh portion into the body tract, the mesh portion being in the retracted position during introduction;
    forming an object supporting surface by moving the elongate member relative to the sheath so the mesh portion expands; and
    supporting the object with the object supporting surface allowing access to a majority of a surface of the object, from an interior of the body tract, while substantially immobilizing the object.

2. The method of claim 1 wherein providing a catheter comprises:
    providing a handle connected to the sheath; and
    providing a handle connected to the elongate member.

3. The method of claim 1 wherein forming the object supporting surface comprises:
    forming a substantially concave-shaped object supporting surface relative to the sheath.

4. The method of claim 1 wherein forming the object supporting surface comprises:
    forming a substantially convex-shaped object supporting surface relative to the sheath.

5. The method of claim 1 wherein the catheter includes two mesh portions operably connected to the sheath, and wherein forming an object supporting surface comprises:
    forming a first object supporting surface with the first mesh portion; and
    forming a second object supporting surface with the second mesh portion, the second object supporting surface generally opposing the first object supporting surface.

6. The method of claim 1 wherein the object is a stone, and further comprising:
    breaking the stone into pieces; and
    using the mesh portion to filter the pieces in the body tract.

7. The method of claim 6 and further comprising:
    sweeping the body tract with the mesh portion to clear the stone pieces from the body tract.

8. The method of claim 1 wherein providing a catheter having a mesh portion comprises:
    providing a catheter having a meshed portion formed of one of:
        a mesh net;
        braided fibers or wires;
        spirally arranged wires or fibers;
        woven fibers or wires; and
        axially arranged fibers or wires.

9. A catheter for treating an object in a body tract, comprising:
    a sheath having a wall, the sheath defining a lumen therethrough and having a first end and a second end;
    a mesh secured to the sheath by having a secured portion of the mesh embedded in the wall of the sheath throughout substantially the entire length of the sheath, the mesh having a first mesh portion movable between a retracted position and an expanded position; and
    an elongate member disposed in the lumen and operably attached to one of the first mesh portion and the sheath such that axial movement of the elongate member within the lumen causes movement of the first mesh portion between the expanded position and the retracted position.

10. A catheter for treating an object in a body tract, comprising:
    a sheath having a wall, the sheath defining a lumen therethrough and having a first end and a second end;
    a mesh secured to the sheath by having a secured portion of the mesh embedded in the wall of the sheath, the mesh having a first mesh portion movable between a retracted position and an expanded position; and
    an elongate member disposed in the lumen and operably attached to one of the first mesh portion and the sheath such that axial movement of the elongate member within the lumen causes movement of the first mesh portion between the expanded position and the retracted position, wherein the mesh includes a second mesh portion movable between a retracted position and an expanded position.

11. A catheter for treating an object in a body tract, comprising:
    a sheath defining a lumen therethrough and having a first end and a second end;
    a first mesh portion coupled to the sheath and movable between a retracted position and an expanded position;
    a second mesh portion coupled to the sheath nearer the first end than the first mesh portion and moveable between a retracted position and an expanded position, the first and second mesh portions each forming an object supporting surface when in the expanded position; and an elongate member disposed in the lumen and operably attached to one of the first mesh portion, the second mesh portion and the sheath such that axial movement of the elongate member within the lumen causes movement of at least one of the first and second mesh portions between the expanded position and the retracted position.

12. The catheter of claim 11 wherein each of the first and second mesh portions comprise one of:

a mesh net;

woven fibers or wires;

braided fibers or wires;

spirally arranged fibers or wires; and axially arranged fibers or wires.

13. The catheter of claim 11 wherein the axial movement of the elongate member causes movement of both the first and second mesh portions between the expanded position and the retracted portion.

14. The catheter of claim 11 and further comprising:

an axial spacer spacing the first and second mesh portions.

15. The catheter of claim 11 wherein, when in the expanded position, the first and second mesh portions form generally opposing object supporting surfaces.

16. The catheter of claim 11 wherein the first and second mesh portions are independently expandable.

17. An expandable device, comprising:

a first sheath defining a first lumen;

a second sheath defining a second lumen, the second sheath being axially moveable within the lumen of the first sheath;

an expandable element coupled to the second sheath and being movable between a retracted position and a radially expanded position;

an elongate member operably attached to one of the second sheath and the expandable element and extending through the second lumen such that axial movement of the elongate member relative to the second sheath causes the expandable element to expand; and wherein the first sheath is axially moveable relative to the second sheath to coaxially overlie a selected portion of the expandable element to selectively control an outer peripheral dimension of the expandable element when in the expanded position.

18. The expandable device of claim 17 and further comprising:

a first handle coupled to a proximal region of the first sheath;

a second handle coupled to a proximal region of the second sheath; and a third handle coupled to a proximal region of the elongate member.

19. The expandable device of claim 17 wherein the first sheath is short relative to the second sheath and located closely proximate the expandable element.

20. A method of treating a stone in a body tract, comprising:

providing a catheter comprising:

a sheath defining a lumen therethrough;

a mesh portion, coupled to the sheath, the mesh portion being movable between a retracted position and an axially expanded position;

an elongate member disposed in the lumen and operably attached to at least one of the mesh portion and the sheath such that axial movement of the elongate member within the lumen causes movement of the mesh portion between the expanded position and the retracted position;

introducing the sheath and the mesh portion into the body tract proximate the stone, the mesh portion being in the retracted position during introduction;

forming a stone immobilizing surface by moving the elongate member relative to the sheath so the mesh portion expands; and bringing the stone and the stone immobilizing surface into contact with one another; and breaking the stone into fragments.

* * * * *